United States Patent
Wang et al.

(10) Patent No.: US 12,419,918 B2
(45) Date of Patent: Sep. 23, 2025

(54) PEDIOCOCCUS ACIDILACTICI CCFM6432 FOR ALLEVIATING DEPRESSION, FOOD FERMENTED THEREBY AND APPLICATION THEREOF

(71) Applicant: Jiangnan University, Wuxi (CN)

(72) Inventors: Gang Wang, Wuxi (CN); Wei Chen, Wuxi (CN); Peijun Tian, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 650 days.

(21) Appl. No.: 17/536,412

(22) Filed: Nov. 29, 2021

(65) Prior Publication Data
US 2022/0072067 A1 Mar. 10, 2022

Related U.S. Application Data

(63) Continuation of application No. PCT/CN2020/092193, filed on May 26, 2020.

(30) Foreign Application Priority Data

May 31, 2019 (CN) .......................... 201910472995.4

(51) Int. Cl.
A23C 9/123 (2006.01)
A23C 11/10 (2021.01)
(Continued)

(52) U.S. Cl.
CPC .......... *A61K 35/744* (2013.01); *A23C 11/106* (2013.01); *A61P 1/00* (2018.01); *A61P 3/04* (2018.01); *A61P 3/10* (2018.01); *A61P 25/24* (2018.01); *A61P 29/00* (2018.01); *C12N 1/205* (2021.05); *A23V 2400/413* (2023.08)

(58) Field of Classification Search
CPC ....... A61K 35/744; A23C 11/106; A61P 1/00; A61P 3/04; A61P 3/10; A61P 25/24; A61P 29/00; C12N 1/205; A23V 2400/413
See application file for complete search history.

(56) References Cited

FOREIGN PATENT DOCUMENTS

| CN | 103764154 A | 4/2014 |
|---|---|---|
| CN | 109182225 A | 1/2019 |

(Continued)

OTHER PUBLICATIONS

FDA, Water for Pharmaceutical Use, Aug. 27, 2014 (Year: 2014).*

(Continued)

*Primary Examiner* — Louise W Humphrey
*Assistant Examiner* — Mary A Crum
(74) *Attorney, Agent, or Firm* — IPro, PLLC; Na Xu

(57) ABSTRACT

The disclosure discloses *P. acidilactici* CCFM6432 for alleviating depression, food fermented thereby and application thereof. The *P. acidilactici* CCFM6432 of the disclosure can be used to prepare food, health-care products and drugs with the functions of resisting depression, resisting inflammation, resisting inflammatory bowel disease, resisting obesity and resisting type I diabetes. The disclosure further provides fermented food. The fermented food is produced by fermentation using the *P. acidilactici* CCFM6432, and the fermented food includes solid food, liquid food, and semi-solid food. The *P. acidilactici* CCFM6432 has very broad application prospects.

6 Claims, 13 Drawing Sheets
Specification includes a Sequence Listing.

(51) Int. Cl.
    *A61K 35/744*    (2015.01)
    *A61P 1/00*    (2006.01)
    *A61P 3/04*    (2006.01)
    *A61P 3/10*    (2006.01)
    *A61P 25/24*    (2006.01)
    *A61P 29/00*    (2006.01)
    *C12N 1/20*    (2006.01)

(56) References Cited

FOREIGN PATENT DOCUMENTS

| | | | |
|---|---|---|---|
| CN | 109803666 A | | 5/2019 |
| JP | 5786297 A | | 5/1982 |
| KR | 20170043036 | * | 4/2017 |
| WO | WO-2017132230 A1 | * | 8/2017 ............. A01K 41/00 |

OTHER PUBLICATIONS

Song et al. "Recent application of probiotics in food and agricultural science." Probiotics 10.1 (2012): 1-34 (Year: 2012).*

Wang, Chao, et al. "Pediococcus acidilactici AS185 attenuates early atherosclerosis development through inhibition of lipid regulation and inflammation in rats." Journal of Functional Foods 60 (2019): 103424 (Year: 2019).*

Barraza-Ortiz, Diego A., et al. "Combination of a probiotic and an antispasmodic increases quality of life and reduces symptoms in patients with irritable bowel syndrome: a pilot study." Digestive Diseases 39.3 (2021): 294-300 (Year: 2021).*

Barathikannan, Kaliyan, et al. "Anti-obesity efficacy of Pediococcus acidilactici MNL5 in Canorhabditis elegans gut model." International Journal of Molecular Sciences 23.3 (2022): 1276 (Year: 2022).*

Cabello-Olmo, Miriam, et al. "Antidiabetic effects of Pediococcus acidilactici pA1c on HFD-induced mice." Nutrients 14.3 (2022): 692 (Year: 2022).*

Pimentel Cordeiro, Jóctan, et al. "Resistance to obesity prevents obesity development without increasing spontaneous physical activity and not directly related to greater metabolic and oxidative capacity." Plos one 17.8 (2022): e0271592 (Year: 2022).*

Zayed, Gaber, and Yrjo H. Roos. "Influence of trehalose and moisture content on survival of Lactobacillus salivarius subjected to freeze-drying and storage." Process Biochemistry 39.9 (2004): 1081-1086. (Year: 2004).*

Appendix A, sequence alignment, 2024 (Year: 2024).*

Kanher, Poonam R., et al. "Lubricants in pharmaceutical solid dosage forms with special emphasis on magnesium stearate." World J. Pharm. Res (2017): 131-146 (Year: 2017).*

Johnson, Jethro S., et al. "Evaluation of 16S rRNA gene sequencing for species and strain-level microbiome analysis." Nature communications 10.1 (2019): 5029 (Year: 2019).*

P. Forsythe W. A. Kunze, "Voices from within: gut microbes and the CNS", Cell. Mol. Life Sci., V70, No. 1,May 27, 2012.

* cited by examiner

SEQUENCE LISTING

<160> NUMBER OF SEQ ID NOS: 5

<210> SEQ ID NO 1
<211> LENGTH: 930

```
<212> TYPE: DNA
<213> ORGANISM: Pediococcus acidilactici

<400> SEQUENCE: 1
ctagctccta aaggttaccc caccggcttt gggtgttaca aactctcatg gtgtgacggg      60
cggtgtgtac aaggcccggg aacgtattca ccgcggcatg ctgatccgcg attactagcg     120
attccgactt cgtgtaggcg agttgcagcc tacagtccga actgagaatg gttttaagag     180
attagctaaa cctcgcggtt cgcaactcg ttgtaccatc cattgtagca cgtgtgtagc      240
ccaggtcata aggggcatga tgatttgacg tcgtccccac cttcctccgg tttgtcaccg     300
gcagtctcac tagagtgccc aactgaatgc tggcaactag taataagggt tgcgctcgtt     360
gcgggactta acccaacatc tcacgacacg agctgacgac aaccatgcac cacctgtcat     420
tctgtccccg aagggaacgc taatctctt aggttggcag aagatgtcaa gacctggtaa     480
ggttcttcgc gtagcttcga attaaaccac atgctccacc gcttgtgcgg gccccgtca    540
attcttttga gtttcaacct tgcggtcgta ctccccaggc ggattactta atgcgttagc     600
tgcagcactg aagggcggaa accctccaac acttagtaat catcgtttac ggcatggact     660
accagggtat ctaatcctgt tcgctaccca tgctttcgag cctcagcgtc agttacagac     720
cagacagccg ccttcgccac tggtgttctt ccatatatct acgcatttca ccgctacaca     780
tggagttcca ctgtcctctt ctgcactcaa gtcccagt ttccaatgca cttcttcggt      840
tgagccgaag ctttcacat tagacttaaa agaccgcctg cgctcgcttt acgcccaata      900
aatcccggat aacgcttggc cacctacgta                                      930

<210> SEQ ID NO 2
<211> LENGTH: 23
<212> TYPE: DNA
<213> ORGANISM: Artificial sequence
<220> FEATURE:
<223> OTHER INFORMATION: Synthetic DNA

<400> SEQUENCE: 2
aacaaagacc attcctccga aag                                              23

<210> SEQ ID NO 3
<211> LENGTH: 23
<212> TYPE: DNA
<213> ORGANISM: Artificial sequence
<220> FEATURE:
<223> OTHER INFORMATION: Synthetic DNA

<400> SEQUENCE: 3
tgtaacaggc tcacatgatt ctc                                              23

<210> SEQ ID NO 4
<211> LENGTH: 23
<212> TYPE: DNA
<213> ORGANISM: Artificial sequence
<220> FEATURE:
<223> OTHER INFORMATION: Synthetic DNA

<400> SEQUENCE: 4
aacaaagacc attcctccga aag                                              23

<210> SEQ ID NO 5
<211> LENGTH: 23
<212> TYPE: DNA
<213> ORGANISM: Artificial sequence
<220> FEATURE:
```

-continued

```
<223> OTHER INFORMATION: Synthetic DNA

<400> SEQUENCE: 5
tgtaacaggc tcacatgatt ctc                                          23
```

PEDIOCOCCUS ACIDILACTICI CCFM6432 FOR ALLEVIATING DEPRESSION, FOOD FERMENTED THEREBY AND APPLICATION THEREOF

REFERENCE TO SEQUENCE LISTING

The instant application contains a Sequence Listing ASCII plan text file format as a file named "seq.txt", created on Sep. 23, 2021, of 4096 bytes in size, and which is hereby incorporated by reference in its entirety.

TECHNICAL FIELD

The disclosure relates to the technical field of microbiology, and particularly relates to *P. acidilactici* CCFM6432 for alleviating depression, food fermented thereby and application thereof.

BACKGROUND

Depression disorder is characterized by significant and lasting depression. Currently, more than 350 million people worldwide suffer from depression disorder, and the incidence has continued to rise in recent years. Currently, antidepressant drugs that are widely used in clinical treatment, such as selective serotonin reuptake inhibitors (SSRI), generally have shortcomings such as slow onset, inconsistent therapeutic effects, and great side effects, causing serious limitations to the treatment of depression.

The human intestine contains more than 1000 kinds of microorganisms, with a total number of about $10^{14}$-$10^{15}$, weighing 1-1.5 kg. The total number of coding genes of these intestinal microorganisms exceeds 3.3 million, which is about 100 times the total number of human coding genes. Therefore, the intestinal microorganisms are considered to be the second genome of the human body. The intestinal microorganism genome and the human genome interact with environmental factors to affect a variety of important physiological functions of a host. Normal communication between the intestinal microbiome and metabolites thereof and the host is necessary to maintain the health of the host. Disorders of intestinal microecology are related to many diseases, including diabetes, obesity, inflammatory bowel disease, neurodegenerative diseases, tumors, etc.

Many clinical studies have shown that there is significant difference between the intestinal microbiome of patients with depression and those of healthy controls, including decreased diversity, decreased abundance of probiotics, etc. In addition, depression is often accompanied by constipation, diarrhea, and other gastrointestinal dysfunction, which may be related to the disorders of the intestinal microbiome and side effects of antidepressants. There is also significant difference between the intestinal microbiome of animals with abnormal neurological functions and those of healthy control animals, which has been confirmed by a variety of depression models, including an olfactory bulbectomy model, a maternal separation model, a social stress model, a chronic unpredictable stress model, etc. These studies all show that the intestinal microbiome plays a vital role in the occurrence and development of depression.

As a dietary supplement, probiotics have been widely accepted by consumers. At present, most of the studies on the function of probiotics are focused on improving the function of the gastrointestinal tract, regulating nutrition metabolism and immunity, etc. A large number of scientific studies and clinical experiments have proved that probiotics can significantly improve constipation, enteritis, lactose intolerance, infection, inflammation, allergies, and glucose and lipid metabolism disorder. With gradual maturity of a "brain-gut axis" theory, use of probiotics to regulate the intestinal microbiome and improve neurological function has become a new method for the treatment of depression. The regulatory effects of certain Bifidobacteria and Lactobacilli on the neurological function have also been confirmed by animal studies and clinical studies, such as *Lactobacillus helveticus* R0052, and *Bifidobacterium longum* R0175.

SUMMARY

The disclosure provides *P. acidilactici* CCFM6432, preserved at the Guangdong Microbial Culture Collection Center on Apr. 25, 2019, the preservation address is Guangdong Institute of Microbiology, 5th Floor, Building 59, Grand Courtyard 100, Xianlie Middle Road, Guangzhou, and the preservation number is GDMCC No. 60638.

In an example, the *P. acidilactici* CCFM6432 has the following characteristics of:
(1) alleviating depression-like behaviors of a depressed individual;
(2) increasing the content of neurotransmitter 5-hydroxytryptamine in the brain of the depressed individual;
(3) promoting biosynthesis of a neurotransmitter precursor 5-hydroxytryptophane in the peripheral tissue of the depressed individual;
(4) inhibiting excessive secretion of corticotropin releasing factors in the hypothalamus of the depressed individual, and reducing the level of corticosterone in the serum of depressed mice, thereby alleviating hyperfunction of the "hypothalamic-pituitary-adrenal axis";
(5) regulating the immunity of a host, increasing the proportion of regulatory T cells in the spleen, and decreasing the concentration of proinflammatory factors IL-1β, IL-6 and TNF-α in the serum; and
(6) improving the diversity of intestinal microbiome of the host, restoring intestinal microbiomemicrobiome disorders caused by stress, increasing the abundance of *Bacillus* and *Coprococcus*, increasing the content of butyric acid in the intestine, and reducing the risk of inflammatory bowel disease, obesity and type II diabetes.

The disclosure further provides a method for preventing or alleviating depression, resisting inflammatory bowel disease, resisting obesity, and resisting type II diabetes. *P. acidilactici* or a probiotic preparation containing *P. acidilactici* CCFM6432 is ingested into the body to achieve the effects of preventing or alleviating depression, resisting inflammatory bowel disease, resisting obesity, and resisting type II diabetes; and the *P. acidilactici* was preserved at the Guangdong Microbial Culture Collection Center on Apr. 25, 2019, with the preservation number of GDMCC No. 60638.

In an example, the prevention or alleviation of depression includes:
(a) alleviating depression-like behaviors of a depressed patient, increasing the content of neurotransmitter 5-hydroxytryptamine in the brain, and promoting biosynthesis of a neurotransmitter precursor 5-hydroxytryptophane in the peripheral tissue; and
(b) inhibiting excessive secretion of corticotropin releasing factors in the hypothalamus, reducing the level of corticosterone in the serum, and alleviating hyperfunction of the "hypothalamic-pituitary-adrenal axis".

In an example, the resistance to inflammation includes:
(a) regulating the immunity of a host;
(b) increasing the proportion of regulatory T cells in the spleen; and
(c) decreasing the concentration of proinflammatory factors IL-1β, IL-6 and/or TNF-α in the serum.

The disclosure further provides a probiotic preparation containing the *P. acidilactici* CCFM6432.

In an example, the concentration of the *P. acidilactici* is greater than or equal to $1\times10^5$ CFU/mL.

In an example, the concentration of the *P. acidilactici* is greater than or equal to $1\times10^5$ CFU/g.

The disclosure further provides fermented food. The fermented food is produced by fermentation using the *P. acidilactici* CCFM6432, and the fermented food includes solid food, liquid food, and semi-solid food.

As an implementation method of the fermented food of the disclosure, the fermented food includes dairy products, bean products, and fruit and vegetable products; the dairy products include milk, sour cream, and cheese; and the fruit and vegetable products include cucumber, carrot, beet, celery, and cabbage products.

In an example, the fermented food is produced by fermentation with the *P. acidilactici* CCFM6432 inoculated at the beginning of fermentation.

The disclosure further provides a drug containing *P. acidilactici* CCFM6432, and the drug further contains a pharmaceutically acceptable carrier and can be used for preventing or alleviating depression, resisting inflammatory bowel disease, resisting obesity, and resisting type II diabetes.

In an example, the dosage form of the drug includes, but is not limited to, tablets, powder or oral liquid.

The disclosure further provides application of the *P. acidilactici* CCFM6432 in preparing a probiotic for colonization in vivo.

In an example, the application is to serve as a host to prepare the probiotic for colonization in vivo.

In an example, the application is to culture the *P. acidilactici* CCFM6432 in an MRS liquid medium at 37° C. for 48 h to obtain a *P. acidilactici* CCFM6432 cell culture solution.

In an example, a probiotic product is prepared by using the cell culture solution.

As a solution for application of the fermented food of the disclosure in preparing antidepressant functional food, the *P. acidilactici* CCFM6432 can alleviate depression-like behaviors of depressed mice, increase the content of neurotransmitter 5-hydroxytryptamine in the brain, and promote biosynthesis of a neurotransmitter precursor 5-hydroxytryptophane in the peripheral tissue; the *P. acidilactici* CCFM6432 can inhibit excessive secretion of corticotropin releasing factors in the hypothalamus, and reduce the level of corticosterone in the serum, thereby alleviating hyperfunction of the "hypothalamic-pituitary-adrenal axis"; the *P. acidilactici* CCFM6432 can regulate the immunity of a host, increase the proportion of regulatory T cells in the spleen, and decrease the concentration of proinflammatory factors IL-1β, IL-6 and TNF-α in the serum; and the *P. acidilactici* CCFM6432 can also improve the diversity of intestinal microbiome of the host, restore intestinal microbiome disorders caused by stress, increase the abundance of *Bacillus* and *Coprococcus*, increase the content of butyric acid in the intestine, and reduce the risk of inflammatory bowel disease, obesity and type II diabetes.

Beneficial effects of the disclosure: in an experiment of depressed model mice, taking the *P. acidilactici* CCFM6432 of the disclosure can alleviate depression-like behaviors of mice caused by stress, increase the content of neurotransmitter (5-HT) in the brain tissue of depressed mice, promote biosynthesis of the neurotransmitter precursor (5-HTP) in the peripheral tissue, inhibit excessive secretion of corticotropin releasing factors (CRF) in the hypothalamus, and reduce the level of corticosterone in the serum; the fermented food can regulate the immunity of the host, increase the proportion of regulatory T cells in the spleen, decrease the concentration of proinflammatory factors IL-1β, IL-6 and TNF-α in the serum; and in addition, the fermented food can improve the diversity of the intestinal microbiome, restore intestinal microbiome disorders caused by stress, increase the abundance of probiotics (*Bacillus* and *Coprococcus*), increase the content of butyric acid in the intestine, and reduce the risk of inflammatory bowel disease, obesity and type II diabetes.

The *P. acidilactici* CCFM6432 of the disclosure can be used to prepare food, health-care products and drugs with the functions of resisting depression, resisting inflammation, resisting inflammatory bowel disease, resisting obesity, resisting type I diabetes, and the like, and has a very wide application prospect.

Biomaterial Preservation

*P. acidilactici* CCFM6432, with a category name of *P. acidilactici*, was preserved at the Guangdong Microbial Culture Collection Center on Apr. 25, 2019, with the preservation number of GDMCC No. 60638.

BRIEF DESCRIPTION OF FIGURES

In order to more clearly illustrate the technical schemes of the examples of the disclosure, the accompanying drawings used in the description of the examples are briefly described below. It is obvious that the accompanying drawings in the following description are only some examples of the disclosure, and other accompanying drawings may be obtained by those skilled in the art based on these accompanying drawings without any creative effort. In the figures.

DETAILED DESCRIPTION

Figure 1:
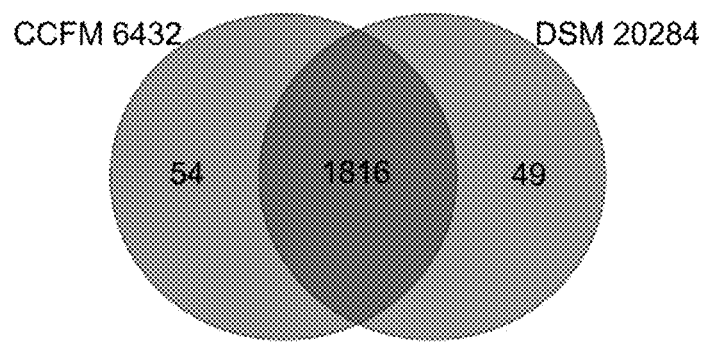
FIG. 1 shows core gene analysis of CCFM6432 and *P. acidilactici* type strain DSM20284.

For the purpose of making the objectives, characteristics and advantages of the disclosure clearer and more understandable, detailed description will be made to the specific implementations of the disclosure in conjunction with specific examples.

In the following description, many specific details are set forth in order to provide a full understanding of the disclosure. However, the disclosure may be implemented in other ways different from those described herein, and those skilled in the art can make similar promotion without violating the connotation of the disclosure. Therefore, the disclosure is not limited by the specific examples disclosed below.

In addition, "an example" or "examples" used herein refer to particular features, structures, or characteristics that are included in at least one implementation mode of the disclosure. "In an example" appearing in different places in this description is not intended to refer to the same example, nor is it a separate or selective example that is mutually exclusive with other examples.

Example 1 Screening of *P. acidilactici*

(I) Isolation and screening of *P. acidilactici* CCFM6432:

(1) 1 g of fresh feces from a healthy person was taken. After gradient dilution, the feces was spread on an mMRS solid medium and cultured in an anaerobic environment at 37° C. for 72 h.

(2) The colonial morphology was observed and recorded, and colonies were picked for purification by streaking.

(3) The colonies were cultured in an MRS liquid medium at 37° C. for 48 h and then subjected to gram staining, and the colonial morphology was recorded.

(4) Gram-negative bacteria and gram-positive cocci were discarded from the colonies, and gram-positive cocci were selected.

(5) After catalase analysis, catalase-positive strains were discarded and catalase-negative strains were kept.

(II) Molecular Biological Identification of *P. acidilactici*:

(1) Single-bacterial genome extraction: the *P. acidilactici* screened in step (I) was cultured overnight. 1 mL of the bacterial suspension cultured overnight was taken in a 1.5 ml centrifuge tube and centrifuged at 10000 rpm for 2 min, and the supernatant was discarded to obtain bacteria. After being blow washed with 1 mL of sterile water, the bacteria were centrifuged at 10000 rpm for 2 min, and the supernatant was discarded to obtain the bacteria. 200 μL of SDS lysate was added, and subjected to water bath at 80° C. for 30 min. 200 μL of a phenol-chloroform solution was added to the bacterial lysate, where the components of the phenol-chloroform solution include Tris saturated phenol, chloroform and isoamyl alcohol in a volume ratio of Tris saturated phenol:chloroform:isoamyl alcohol=25:24:1. After being mixed upside down, the mixed solution was centrifuged at 12000 rpm for 5-10 min, and 200 μL of supernatant was taken. 400 μL of ice ethanol or ice isopropanol was added to the 200 μL of supernatant, the mixed solution was enabled to stand at −20° C. for 1 h, and centrifuged at 12000 rpm for 5-10 min, and the supernatant was discarded. 500 μL of 70% (volume percentage) ice ethanol was added to resuspend precipitates, the resuspension was centrifuged at 12000 rpm for 1-3 min, and the supernatant was discarded. The centrifugate was dried in an oven at 60° C., or air dried. 50 μL of ddH$_2$O was added to redissolve the precipitates for PCR.

(2) 16S rDNA PCR:

A. 50 μL PCR reaction system of 16S rDNA of bacteria: 10×Taq buffer, 5 μL; dNTP, 5 μL; 27F, 0.5 μL; 1492R, 0.5 μL; Taq enzyme, 0.5 μL; template, 0.5 μL; ddH$_2$O, 38 μL.

B. PCR conditions: 95° C., 5 min; 95° C., 10 s; 55° C., 30 s; 72° C., 30 s; steps 2-4, 30×; 72° C., 5 min; 12° C., 2 min.

C. 1% agarose gel was prepared, and then a PCR product was mixed with a 10000× loading buffer. The loading quantity of sample was 2 μL, agarose gel electrophoresis was performed for 30 min at 120 V, and then gel imaging was performed.

D. The obtained PCR product was sent to a professional sequencing company. The sequencing result (as shown in SEQ ID NO.1) was subjected to search and similarity comparison in GenBank using BLAST, and the strain was identified as *P. acidilactici*.

(3) Whole Genome Sequencing

The extracted whole genome was sent to the professional sequencing company, and the whole genome of the bacteria was sequenced using a second-generation sequencer. The sequence result was subjected to search and similarity comparison in GeneBank using BLAST, and the sequencing result was that the strain was identified as a newly discovered strain belonging to *P. acidilactici*. The strain was preserved at −80° C. for later use. The results of comparative genome analysis with the type strain *P. acidilactici* DSM 20284 are shown in Table 1. The results of core gene analysis are shown in FIG. 1. The number of core genes shared by the two strains is 1816; the number of unique genes of CCFM6432 is 54; and the number of unique genes of DSM20284 is 49.

TABLE 1

Results of comparative genome analysis with type strain *P. acidilactici* DSM 20284

| Strains | Genome size/Mbp | Gene number | Gene average length/bp | GC content/% |
|---|---|---|---|---|
| CCFM6432 | 1.93 | 1888 | 894 | 42.11 |
| DSM 20284 | 1.94 | 1884 | 903 | 42.20 |

(III) By research on the biological characteristics of the *P. acidilactici* CCFM6432, the results show that the *P. acidilactici* CCFM6432 has the following biological characteristics:

(1) bacterial characteristics: gram-positive, non-spore-forming, and inactive;

(2) colony characteristics: milky white, round, neat, slightly convex, opaque, and moist and smooth in the surface; and (3) growth properties: the lowest growth temperature of the strain is 15° C. and the highest growth temperature is 45° C.; the best growth temperature is 35-37° C.; the optimum growth pH is 6.5; and the strain enters a stationary phase after being cultured for 18 h.

Example 2: *P. acidilactici* CCFM6432 Reduces Depression-Like Behaviors of Mice 32 6-week-old male C57BL/6J mice were selected. After one week of adaptation to the environment, the mice were randomly divided into four groups according to body weight: a normal control group, a depression model group, a drug intervention group, and a CCFM6432 intervention group, each containing 8 mice. Animal grouping and treatment methods are shown in Table 2.

TABLE 2

Animal experiment grouping and treatment methods

| Group | Treatment method | Experimental period |
|---|---|---|
| Normal control group | Free diet and water, gavage with a control solvent | 6 weeks |
| Depression model group | Chronic unpredictable mild stress; free diet and water, gavage with a control solvent | 6 weeks |
| Drug control group | Chronic unpredictable mild stress; free diet and water, gavage with 10 mg/kg fluoxetine | 6 weeks |
| CCFM6432 intervention group | Chronic unpredictable mild stress; free diet and water, gavage with $10^9$ cfu of live lactic acid bacteria | 6 weeks |

Chronic unpredictable stress depression mouse model: 1-2 kinds of stimuli were randomly performed every day, and the performance time of stimuli every day was determined randomly to avoid the circadian rhythm. Each method was used for not more than three times, and the stimuli were performed for five weeks. The stimuli include: (1) fasting for 24 h; (2) water deprivation+empty bottle stimulus for 24 h; (3) tail pinching for 3 min; (4) wet padding for 24 h; (5) immobilization for 1-2 h; (6) 45° tilted cage for 24 h; (7) continuous lighting for 24 h; (8) no padding for 24 h; (9) forced swim for 15 min; and (10) separation for 24 h.

Lactic acid bacteria gavage: the activated second generation of *P. acidilactici* CCFM6432 was taken and cultured at 37° C. for 24 h, and the bacteria were collected after centrifugation at 4° C. and 8000 r/min for 3 min. The supernatant was discarded and the bacteria were resuspended with 5% sterilized skim milk to make the concentration of lactic acid bacteria reach $5\times10^9$ CFU/mL. The gavage volume was 0.2 mL/mouse/day.

From the fifth week, the daily chronic unpredictable stress and intervention of drugs and probiotics were stopped, and behavioral tests were conducted on all mice, including elevated plus-maze test, tail suspension test, and sucrose preference test. The specific implementation methods and results are as follows:

(1) Elevated Plus-Maze Test

Figure 2A:
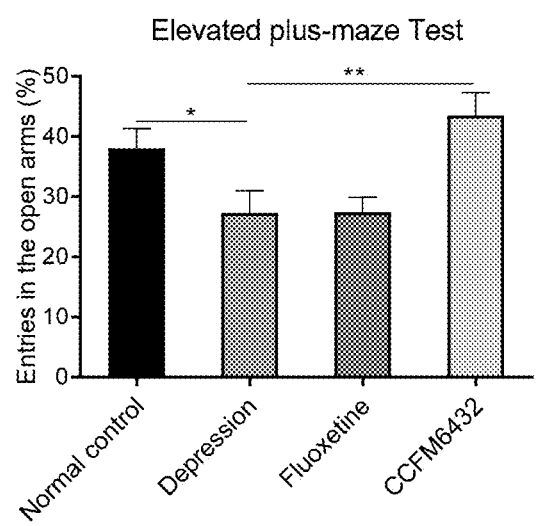
FIG. 2A shows the number of entries in open arms of mice in an elevated plus maze, where $*P<0.05$, $**P<0.01$.
Figure 2B:
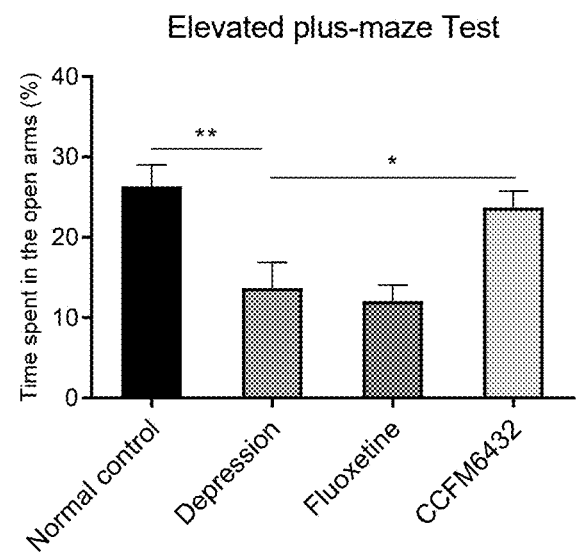
FIG. 2B shows time spent in open arms of mice in an elevated plus maze, where $*P<0.05$, $**P<0.01$.
Figure 2C:
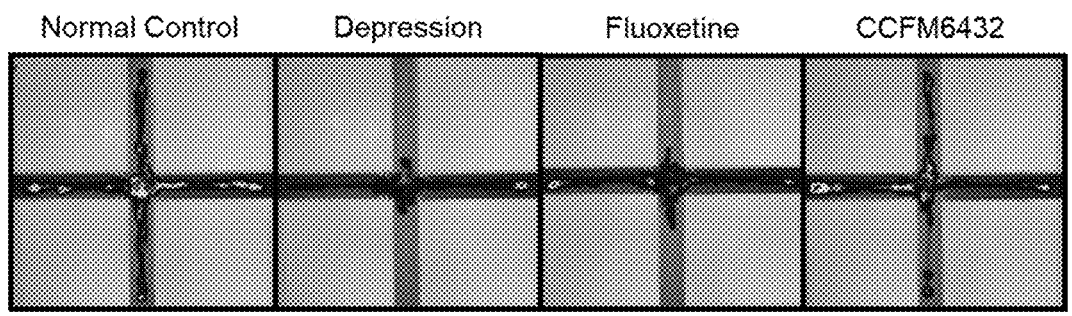
FIG. 2C shows movement tracks of mice in a plus maze, where $*P<0.05$, $**P<0.01$.

At the beginning of the test, a mouse was placed into a maze from the central grid facing a closed arm, and its activities within 10 min were recorded. Observation indicators include: entries in the open arms (two forepaws must enter the arm), time spent in the open arms, entries in the closed arms, and time spent in the closed arms. The proportion of time spent in the open arms, the proportion of entries in the open arms, and the total number of entries in the elevated plus maze were calculated. After the test, the mouse was taken out, the arms were cleaned, alcohol was sprayed to remove the odor, and test of the next mouse was performed. The results are shown in FIG. 2. The entries and time spent in the open arms of the depressed mice were significantly reduced. Taking CCFM6432 could significantly improve the symptom. Fluoxetine had no effect on the depression-like behaviors of the mice in the plus maze.

(2) Tail Suspension Test

Figure 3A:
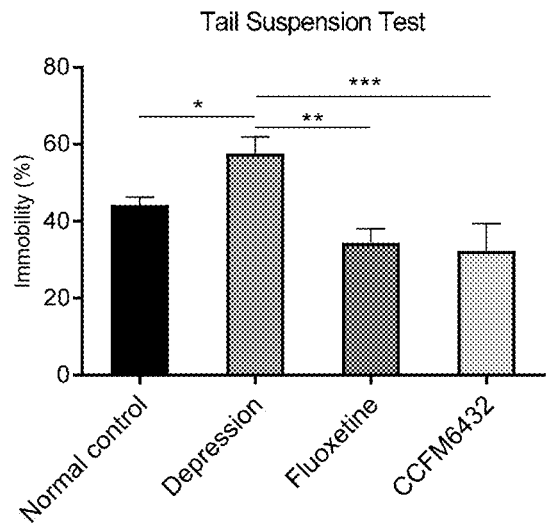
FIG. 3A shows time of immobility of mice in a tail suspension test, where $*P<0.05$, $P<0.01$, $*P<0.001$.

The tail suspension test is similar to the forced swim test, and is also a behavioral despair model. The rear ⅓ part of the tail of a mouse was fixed with adhesive tape and hung on a bracket; the head was 30 cm away from a table; and the mouse was videoed with a camera. The background of the camera was in obvious contrast with the coat color of the mouse. Timing was stopped after 6 min, and the immobility time of the mouse in the last 4 min (3-6 min) was counted using small animal behavior analysis software. An immobile state means that the animal gives up actively struggling and is in a completely immobile state. The test results are shown in FIG. 3A. The time that the depressed mice were immobile during the tail suspension test increased significantly, while taking CCFM6432 could reduce the immobility time and alleviate the depressive state of the depressed mice, and the effect of the CCFM6432 was better than that of the antidepressant fluoxetine.

(3) Sucrose Preference Test

Figure 3B:
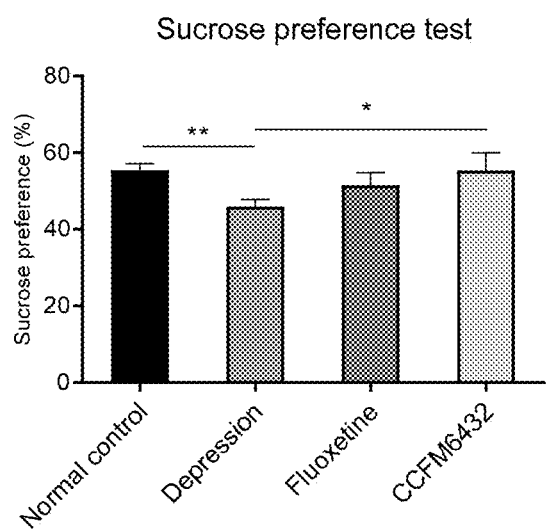
FIG. 3B shows ratios of consumption of sucrose of mice in a sucrose preference test, where $*P<0.05$, $P<0.01$, $*P<0.001$.

The sucrose preference test is a model for testing anhedonia in depression. Before starting the test, two identical drinking bottles were placed in a cage to allow the mice to drink adaptively for at least 3 days. After the adaptation, one of the bottles of water was replaced with an aqueous solution containing 1% sucrose. The intakes of water and sucrose solution were measured by weighing the bottles. The positions of the two bottles were changed every day to reduce drinking preferences due to different amounts of water. A formula for calculating sucrose preference is: sucrose preference=V (sucrose solution)/[V (sucrose solution)+V (water)]×100%. The test lasted for a total of 3 days, and the average value was taken. As shown by the test results in FIG. 3B, the depressed mice had a significant decrease in sucrose preference. After taking the CCFM6432, the mice restored their normal sucrose preference, which indicates that CCFM6432 could alleviate the anhedonia caused by depression.

Figure 4A:
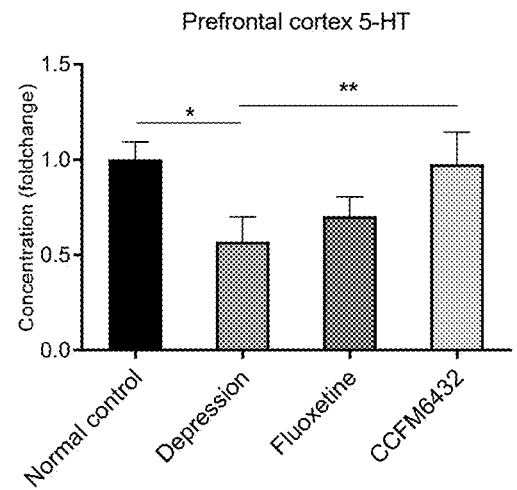
FIG. 4A shows the concentration of 5-HT in the prefrontal cortex of mice, where $*P<0.05$, $****P<0.0001$.
Figure 4B:
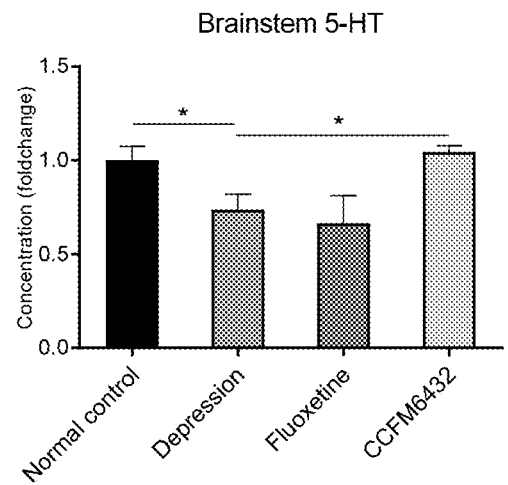
FIG. 4B shows the concentration of 5-HT in the brainstem of mice, where $*P<0.05$, $****P<0.0001$.

Example 3: CCFM6432 Increases the Level of Neurotransmitter (5-HT) in the Brain of Depressed Mice The mice in Example 2 were euthanized at the sixth weekend. The brain tissue of the mice was taken, and the brainstem and the prefrontal cortex were separated on ice. A certain amount of fresh brainstem and prefrontal cortex tissue (not less than 50 mg by weight) was separately taken. 9 times of a sterile PBS buffer by volume (equal to that 9 ml of homogenate was added to 1 g of tissue) was added, and the homogenate was homogenized with a tissue homogenizer. After the tissue fluid was centrifuged at 3000 g for 20 min, the supernatant was taken, an equal volume of 5% perchloric acid was added to precipitate protein, and the solution was centrifuged at 10000 g for 10 min. The supernatant was pipetted and filtered through a 0.22 µm water-based filter membrane, and then the content of 5-HT was measured with an ELISA kit. The test results are shown in FIG. 4. The results show that taking CCFM6432 could significantly reverse the decrease in the level of 5-HT in the brainstem and the prefrontal cortex caused by chronic stress. Among them, CCFM6432 improved 5-HT in the brainstem and the prefrontal cortex to an extent greater than fluoxetine. Study reports show that, as a selective 5-HT reuptake inhibitor, fluoxetine has inconsistencies in the ability to act in different individuals, and has a latency of 2-4 week to take effect. The results of the test show that after the *P. acidilactici* CCFM6432 was taken for five weeks, the content of 5-HT in the brain could be significantly increased, the latency of taking effect is avoided, and the *P. acidilactici* CCFM6432 shows a good potential for antidepressant treatment.

Example 4: *P. acidilactici* CCFM6432 Stimulates Enterochromaffin Cells to Secrete 5-HTP Determination of 5-HTP in cell supernatant: RIN14B cells were inoculated in a 24-well plate at the density of $4\times10^5$/mL and incubated for 72 h. The medium was discarded, the cells were washed with HBSS (1 mL) containing 0.1% bovine serum albumin (BSA) and 2 µM fluoxetine, and 1 mL of an HBSS suspension containing CCFM6432 was added (the control group used HBSS without bacteria). The cells were incubated at 37° C. for 20 min, the supernatant was collected and centrifuged at 6000 g for 5 min to remove precipitate, and the supernatant was frozen at −80° C. for testing. 5-HTP in the cell supernatant was measured by HPLC-FLD (referring to Example 3).

Determination of mRNA of tryptophan hydroxylase 1 (Tph1): adherent cells in the above step were washed three times with HBSS, 1 mL of Trizol was added, and the cells were incubated on ice for 5-10 min. The cells were detached by blowing and patting, and the lysate was transferred to an enzyme-free EP tube. The total cell RNA was extracted by a conventional method, and cDNA synthesis was performed according to instructions of a reverse transcription kit (Prime Script RT reagent Kit gDNA Eraser, Takara). The synthesized cDNA sample was tested for the concentration and purity (A260/A280) by an ultra-micro spectrophotometer (NanoDrop 2000C), and stored at −80° C. for later use. The sample was mixed with a fluorescent dye SYBR Green super mix (Qiagen, Germany). The PCR system contained 5 µL of mix, 1 µL of cDNA, and 1 µL of forward and reverse primers, and dd water was used to make up the total volume to 10 µL. Detection was performed on a real-time fluorescent quantitative gene amplification instrument CFX96™ Real-Time System (Bio-Rad, USA). 3 parallel holes were set up for each sample, and a housekeeping gene β-Actin was used as an internal reference. The results obtained were analyzed by a $2^{-\Delta\Delta Cq}$ method; and the primer sequences used are shown in Table 3.

TABLE 3

QPCR primer sequence

| Gene | Sequence | Nucleotide sequence |
|---|---|---|
| Tph1 | F-5'-AACAAAGACCATTCCTCCGAAAG-3' | SEQ ID NO. 2 |
|  | R-5'-TGTAACAGGCTCACATGATTCTC-3' | SEQ ID NO. 3 |
| GAPDH | F-5'-AACAAAGACCATTCCTCCGAAAG-3' | SEQ ID NO. 4 |
|  | R-5'-TGTAACAGGCTCACATGATTCTC-3' | SEQ ID NO. 5 |

Figure 5A:
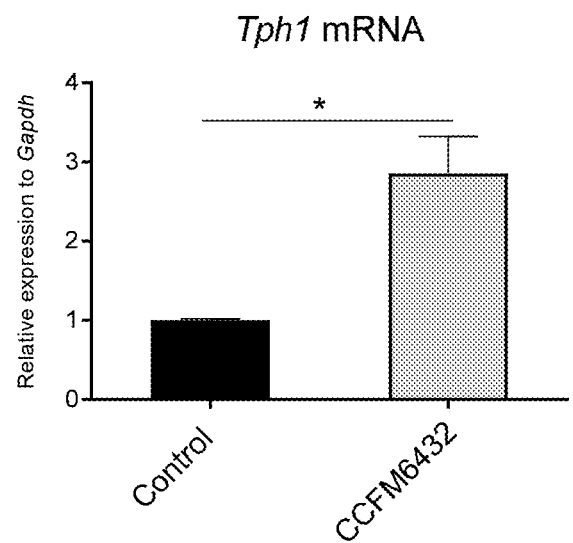
FIG. 5A shows the expression of tryptophan hydroxylase 1 (Tph1) mRNA in the intestinal enterochromaffin cells of mice, where $*P<0.05$, $****P<0.0001$.
Figure 5B:
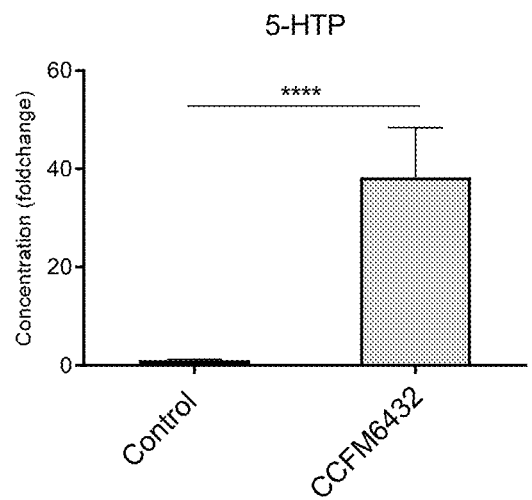
FIG. 5B shows the content of 5-HTP secreted by the intestinal enterochromaffin cells of mice, where $*P<0.05$, $****P<0.0001$.

The results (FIG. 5) show that after the CCFM6432 stimulated the RIN14B cells, the mRNA level of Tph1 in the cells was significantly increased by 2.5 times and nearly 40 times respectively. Correspondingly, the amount of 5-HTP secreted by the cells was also significantly increased. The 5-HTP secreted by the enterochromaffin cells can enter blood circulation and pass through a blood-brain barrier to provide a precursor substance for the synthesis of 5-HT in the brain. Therefore, the CCFM6432 can specifically stimulate the secretion of 5-HTP from enterochromaffin cells to promote the synthesis of 5-HT in the brain and achieve an antidepressant function.

Figure 6A:
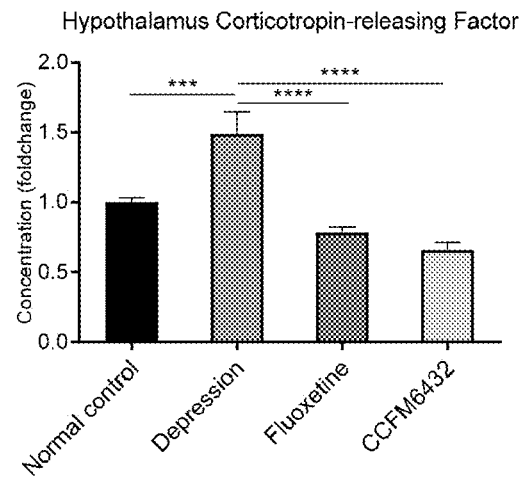
FIG. 6A shows the level of corticotropin releasing factors in the hypothalamus of mice, where $*P<0.05$, $P<0.01$, $*P<0.001$.
Figure 6B:
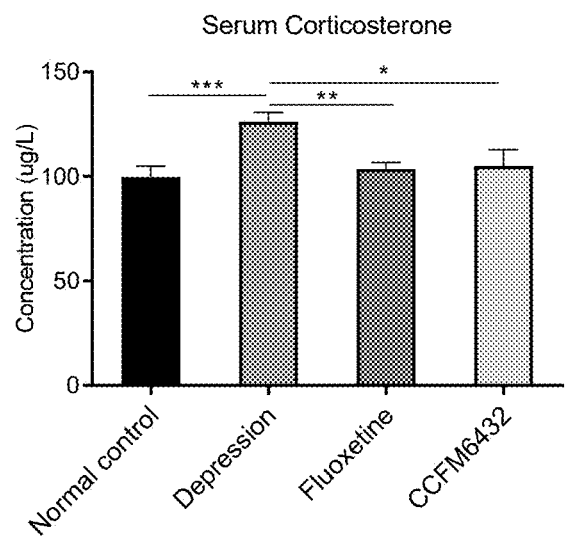
FIG. 6B shows the level of corticosterone in the serum of mice, where $*P<0.05$, $P<0.01$, $*P<0.001$.

Example 5: *P. acidilactici* CCFM6432 can Alleviate HPA Hyperfunction in Depressed Mice The mice in Example 2 were euthanized at the sixth weekend, and the blood of the mice was collected and centrifuged at 1000 g for 15 min to obtain serum. The mouse brain tissue was taken, and the hypothalamus was separated on ice to prepare a tissue homogenate (referring to Example 2). The content of corticosterone in the serum and the content of corticotropin releasing factors (CRF) in the hypothalamus were measured using an ELISA kit. The test results (FIG. 6) show that due to continuous chronic stress, the depressed mice had hyperfunction of the hypothalamus-pituitary-adrenal axis (HPA), the CRF released by the hypothalamus increased significantly, and the concentration of corticosterone in the serum increased significantly. Taking CCFM6432 could significantly inhibit the release of CRF and reduce the level of corticosterone in the serum, thereby alleviating HPA hyperactivity. CCFM6432 shows good antidepressant effects.

Figure 7:
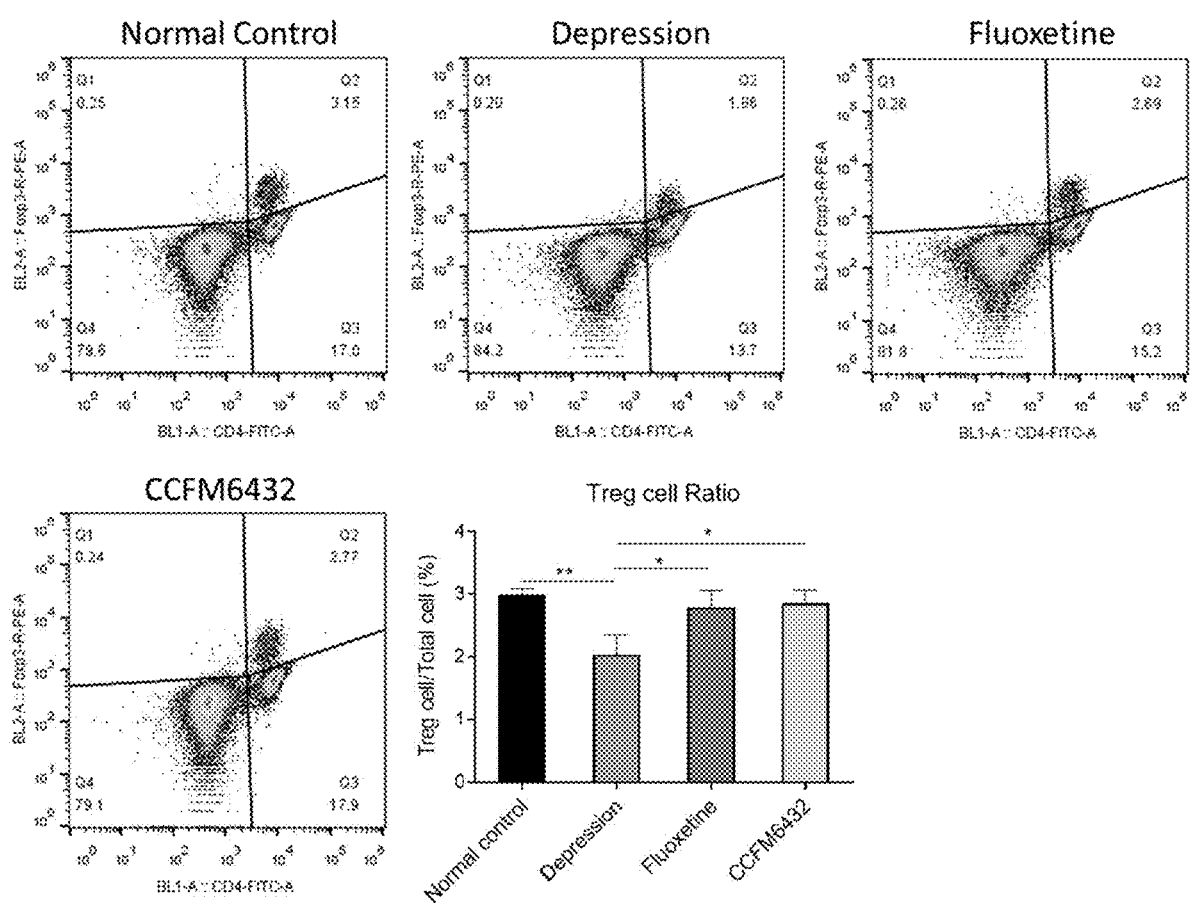
FIG. 7 shows the effect of CCFM6432 on the proportion of regulatory T cells in the spleen of depressed mice, where *P<0.05, **P<0.01.
Figure 8A:
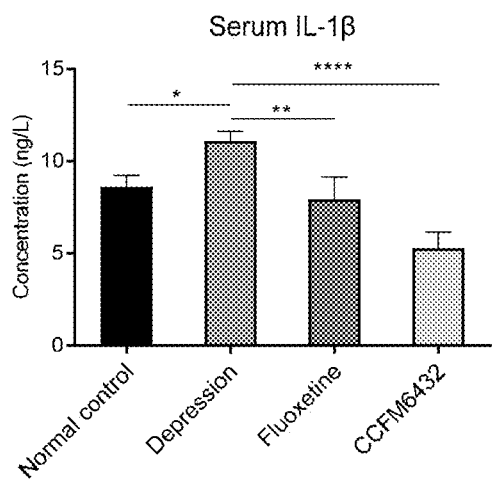
FIG. 8A shows the content of IL-1B in the serum of mice.
Figure 8B:
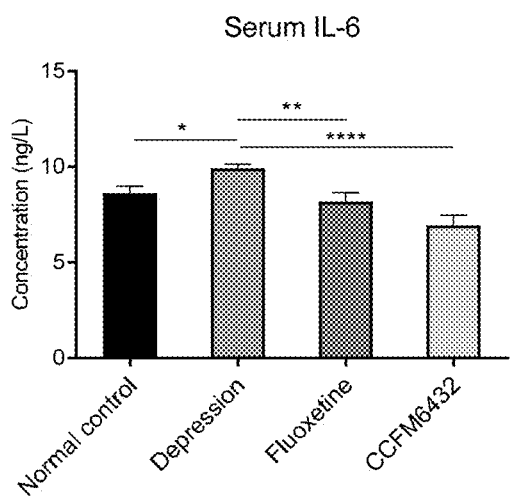
FIG. 8B shows the content of IL-6 in the serum of mice.
Figure 8C:
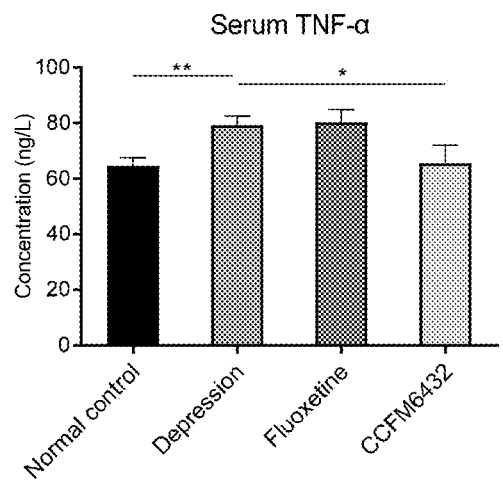
FIG. 8C shows the content of TNF-α in the serum.

Example 6: *P. acidilactici* has an Immunomodulatory Effect on Depressed Mice The mice in Example 2 were euthanized at the sixth weekend. A fresh mouse spleen (about 50 mg) was taken, 5 mL of a pre-chilled PBS buffer was added, and the mouse spleen was cut, ground, and filtered with a 200-mesh nylon sieve to obtain a tissue cell suspension. 2 mL of an erythrocyte lysate was added for lysis for 4 min, and the lysate was removed by centrifugation at room temperature (300×g, 5 min). The obtained cell precipitate was washed with pre-cooled PBS twice, and resuspended with a certain amount of PBS to obtain a lymphocyte suspension. Antibody labeling of regulatory T cells (Tregs) was performed in accordance with the instructions of an eBioscience Mouse Regulatory T cell Staining Kit (Invitrogen Corporation, Carlsbad, CA, USA). The Tregs (CD4+CD25+Foxp3+) were detected by flow cytometry. The contents of IL-1β, IL-6 and TNF-α in the serum were detected with an ELISA kit. The test results are shown in FIG. 7. Chronic stress could significantly reduce the proportion of Tregs in the mouse spleens, and impair the immunity of the mice. At the same time, the contents of pro-inflammatory factors IL-1β, IL-6 and TNF-α in the serum of the mice increased significantly (FIG. 8), which indicates that the depressed mice were accompanied by systemic inflammation. Both fluoxetine and the CCFM6432 could significantly improve the immune state of the depressed mice and reduce the degree of inflammation. In particular, compared with fluoxetine, taking CCFM6432 could significantly reduce the content of TNF-α in the serum and had a better anti-inflammatory effect.

Figure 9A:
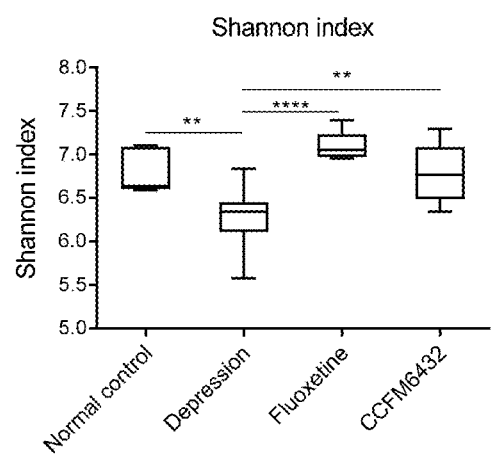
FIG. 9A shows the Shannon index of the intestinal microbiomes of mice, where P<0.01, *P<0.001.
Figure 9B:
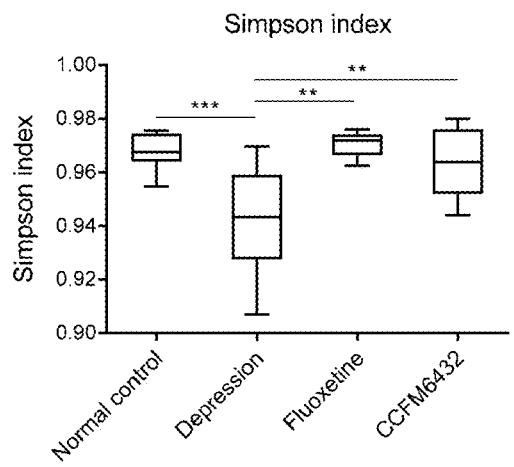
FIG. 9B shows the Simpson index of the intestinal microbiome of mice, where P<0.01, *P<0.001.
Figure 9C:
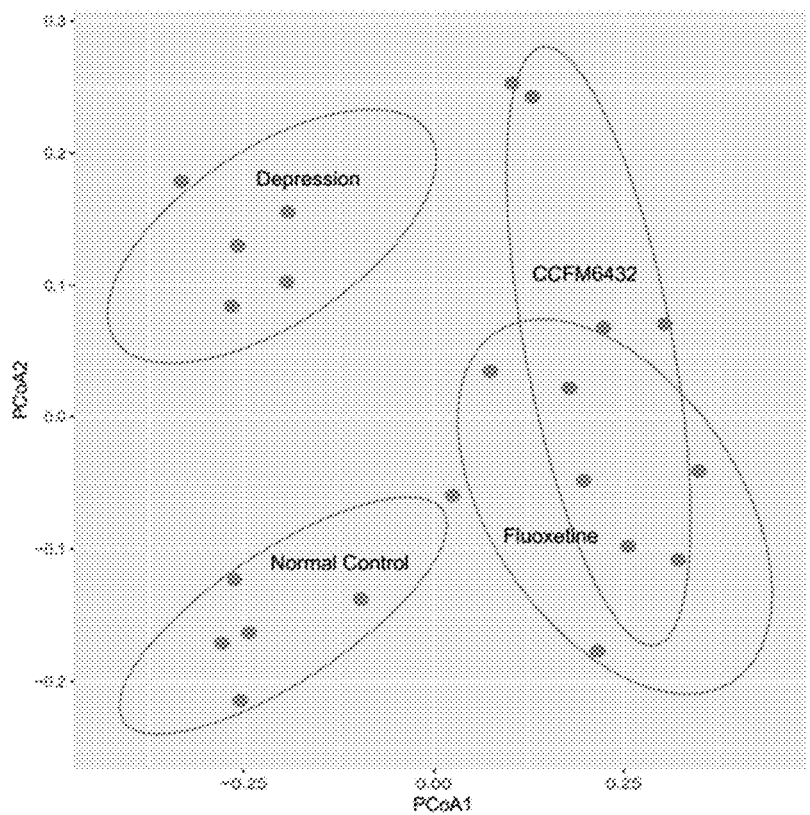
FIG. 9C shows a scatter diagram of PCoA of the intestinal microbiome of mice, where P<0.01, *P<0.001.
Figure 9D:
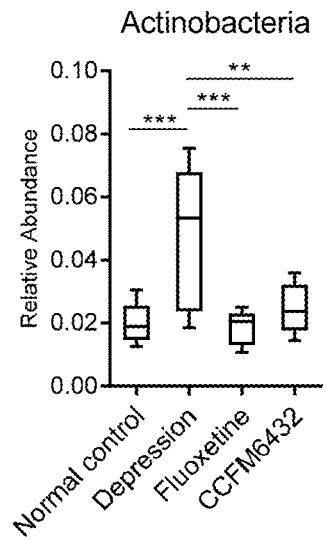
FIG. 9D shows the abundance of Actinobacteria in the intestinal microbiome of mice, where P<0.01, *P<0.001.
Figure 9E:
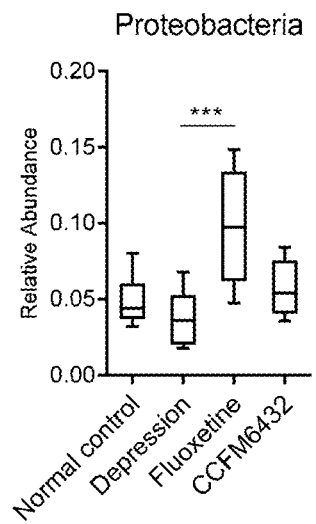
FIG. 9E shows the abundance of Proteobacteria in the intestinal microbiome of mice, where P<0.01, *P<0.001.
Figure 9F:
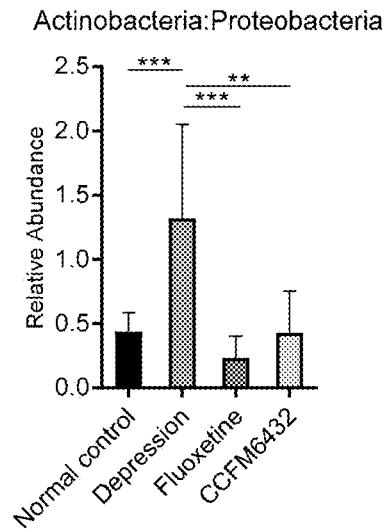
FIG. 9F shows the ratio of Actinobacteria to Proteobacteria in the intestinal microbiome of mice, where P<0.01, *P<0.001.
Figure 10A:
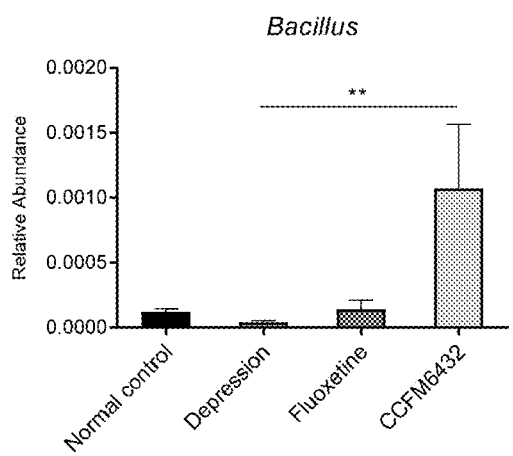
FIG. 10A shows the abundance of *Bacillus* in the intestine of mice, where *P<0.05, **P<0.01.
Figure 10B:
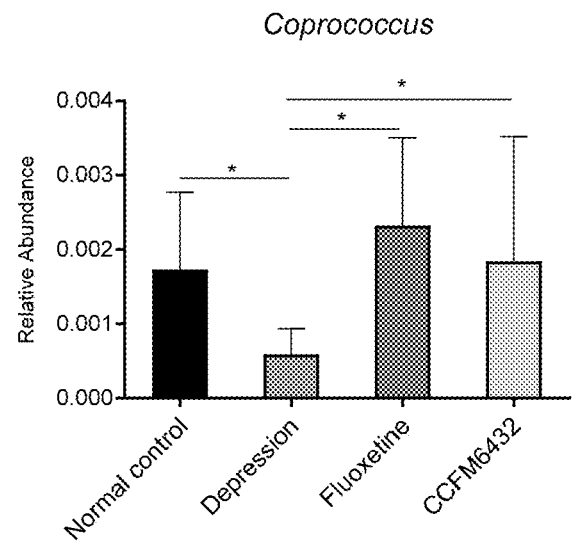
FIG. 10B shows the abundance of *Coprococcus* in the intestine of mice, where *P<0.05, **P<0.01.

Example 7: *P. acidilactici* CCFM6432 Regulates the Intestinal Microbiome and Metabolites of Depressed Mice Fresh feces of the mice in Example 2 was taken at the sixth weekend, and total DNA was extracted from the mouse feces sample using an MP feces kit. Specific operation steps are as follows, mainly referring to the kit instructions. The mouse fecal genome was used as a template, V3-V4 fragments of 16S rDNA were amplified using a forward primer 520F (5'-AYTGGGYDTAAAGNG-3') and a reverse primer 802R (5'-TACNVGGGTATCTAATCC-3') as primers, and the length of a target fragment was about 247 bp. After the PCR reaction, all PCR samples in which target bands were observed were electrophoresed again, a 2.0% agarose gel was prepared, and electrophoresis was performed at 120 V for 40 min. After electrophoresis, the target bands were quickly cut under a UV lamp. The target band gel was extracted according to the instructions of a QIAquick Gel Extraction Kit. The DNA concentration of the sample was measured according to a Qubit DNA3.0 kit, then a library was constructed according to a TurSeq DNA LT Sample Preparation Kit and instructions thereof, and finally determination was performed on an Illumina Miseq sequencer according to a MiSeq Regent Kit and instructions thereof. After sequencing, sequences with the length smaller than 200 bp, primer sequences, and a single sequence that cannot be assembled were removed, and sequences were assembled according to a standard that overlapping bases are greater than 10 bp without mismatches. The sequences with the similarity greater than 97% were defined as a taxonomic unit (Operational Taxonomic Unit, OTU), and the species was determined by a Ribosomal Database Project (RDP) Naïve Bayesclassifier. The α-diversity and β-diversity of the sample were calculated to assess the bacterial diversity of the sample. Among them, the α-diversity is characterized by Shannon index and Simpson index. The results (FIGS. 9A, B) show that the intestinal microbiome of the depressed mice had decreased α-diversity, which indicates that depression was accompanied by a certain degree of intestinal microbiome disorder. Taking the CCFM6432 could significantly up-regulate the α-diversity of the intestinal microbiome and improve the species abundance and uniformity of the intestinal microbiome. In terms of the phylum level, the structure of the intestinal microbiome of the depressed mice was significantly different from that of normal mice, especially the abundance of Proteobacteria and Actinobacteria. The abundance of Actinobacteria in the depressed mice increased, and the ratio of the Actinobacteria to the Proteobacteria increased significantly. Taking CCFM6432 could significantly reverse the phenomenon and restore the structure of the intestinal microbiome to normal (FIGS. 9D, E, F). The β-diversity was assessed by principal co-ordinates analysis (PCoA) (FIG. 9C). From the results, both fluoxetine and CCFM6432 intervention could normalize the structure of the intestinal microbiome of the mice. In addition, taking the CCFM6432 could significantly increase the abundance of *Bacillus* (FIG. 10A). *Bacillus* is an important type of lactic acid-producing bacteria in the host, and plays a very important role in maintaining normal intestinal peristalsis and alleviating constipation. In addition, some species of *Bacillus* (such as *Bacillus coagulans* and *Bacillus subtilis*) can secrete bacteriocins, inhibit the growth of enteropathogenic bacteria, and prevent the occurrence of inflammatory bowel disease (IBD). Taking CCFM6432 could also significantly increase the abundance of *Coprococcus* in the intestine of the depressed mice (FIG. 10B). *Coprococcus* is an important butyric acid-producing bacterium in the intestine. Butyric acid can supply energy for oxidation of intestinal epithelial cells, improve the intestinal barrier function, maintain immune homeostasis of intestinal mucosa, induce expression of downstream regulatory factors of glucose and lipid metabolism, such as glucagon-like polypeptide-1 (GLP-1) and peptide YY (PYY), through two signaling pathways: a G protein-coupled receptors (GPCRs) activation pathway and a histone deacetylases (HDACs) inhibition pathway, and has a significant improvement effect on type II diabetes and obesity.

Figure 10C:
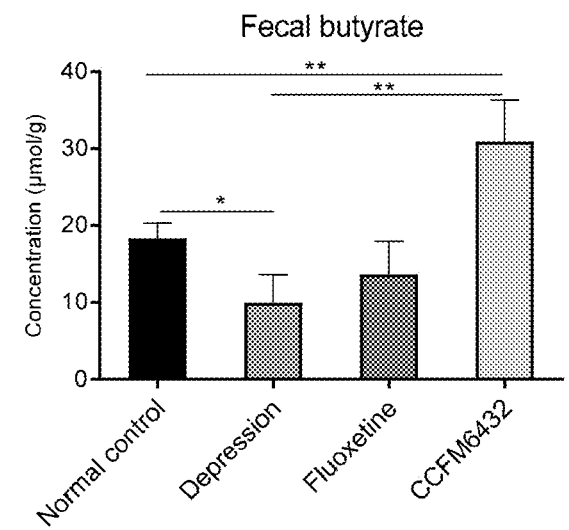
FIG. 10C shows the content of butyric acid in the feces of mice, where *P<0.05, **P<0.01.

To verify the effect of changes in the intestinal microbiome on the content of butyric acid in the intestine, a corresponding mouse fecal sample was taken. 500 μL of saturated NaCl was added and uniformly shaken; 40 μL of 10% sulfuric acid was added and uniformly shaken; 1 mL of ether was added and uniformly shaken; and the mixture was centrifuged at 18000 g at 4° C. for 15 min. The supernatant was taken into a 2 mL EP tube and 0.25 g of anhydrous sodium sulfate was added. The mixture was centrifuged at 18000 g at 4° C. for 15 min. 500 μL of supernatant was taken into a gas phase vial, and the contents of short-chain fatty acids (acetic acid, butyric acid, isobutyric acid, butyric acid and the like) were measured by GC-MS using selective ion scanning. The results in FIG. 10C show that taking *P. acidilactici* CCFM6432 could improve the decrease in butyric acid levels caused by depression, and further prove that the CCFM6432 could not only alleviate depression, but also exert the effects of alleviating and preventing type II diabetes, obesity and other diseases by regulating the content of butyric acid in the intestine.

Example 8

Cryopreserved *P. acidilactici* CCFM6432 was inoculated into an mMRS medium (MRS medium+0.05% cysteine hydrochloride), and cultured anaerobically at 37° C. for 48 h. After subculturing 2-3 times in the mMRS medium, 1 mL of *P. acidilactici* CCFM6432 culture solution was mixed with 9.0 ml of artificial simulated gastric juice with the pH of 2.5 (an mMRS medium containing 1% pepsin, with the pH of 2.5), and cultured anaerobically at 37° C. Samples were taken at 0 h, 0.5 h, 1 h and 2 h respectively, and plate colony counting was performed by pouring and culturing with an mMRS agar medium to determine the number of viable bacteria and calculate the survival rate.

The survival rate is the ratio of the logarithm of the number of viable bacteria at the time of sampling to the logarithm of the number of viable bacteria at the 0th hour in the culture solution, expressed in %. 1 mL of *P. acidilactici* CCFM6432 culture solution was mixed with 9 mL of artificial simulated intestinal juice (an mMRS medium containing 0.3% bovine bile salt, and 1% trypsin, with the pH of 8.0), and cultured anaerobically at 37° C. Samples were taken at 0 h, 0.5 h, 1 h and 2 h respectively, and plate colony counting was performed by pouring and culturing with an mMRS agar medium to determine the number of viable bacteria and calculate the survival rate. The survival rate is the ratio of the logarithm of the number of viable bacteria at the time of sampling to the logarithm of the number of viable bacteria at the 0th hour in the culture solution, expressed in %. The test results are shown in Table 4 and Table 5. The results show that P. acidilactici CCFM6432 had good tolerance to artificial gastrointestinal juice.

TABLE 4

Tolerance of P. acidilactici CCFM6432 in artificial simulated gastric juice

| | Artificial simulated gastric juice | | |
|---|---|---|---|
| Treatment time (h) | 0.5 | 1 | 2 |
| Survival rate (%) | 95.67 | 80.54 | 65.68 |

TABLE 5

Tolerance of P. acidilactici CCFM6432 in artificial simulated intestinal juice

| | Artificial simulated intestinal juice | | | | |
|---|---|---|---|---|---|
| Treatment time (h) | 0.5 | 1 | 2 | 3 | 4 |
| Survival rate (%) | 99.34 | 95.36 | 90.18 | 88.25 | 75.68 |

Example 9: Preparation of Fermented Food Using the P. acidilactici CCFM6432 of the Disclosure Fresh vegetables were washed and juiced, and the juice was subjected to high-temperature instant sterilization. After high-temperature sterilization was performed at 140° C. for 2 s, the temperature was immediately reduced to 37° C., and the juice was inoculated with a P. acidilactici CCFM6432 bacterial starter prepared by the disclosure to make the concentration reach $10^8$ CFU/mL or above. The juice was stored under refrigeration at 4° C., thereby obtaining a fruit and vegetable beverage containing the live P. acidilactici CCFM6432 of the disclosure.

The disclosure can use the P. acidilactici CCFM6432 to produce other fermented food by fermentation, including solid food, liquid food, and semi-solid food. The fermented food includes dairy products, bean products, and fruit and vegetable products; the dairy products include milk, sour cream, and cheese; and the fruit and vegetable products include cucumber, carrot, beet, celery, and cabbage products.

Example 10: Preparation of Drugs Using the P. acidilactici CCFM6432 of the Disclosure A single colony of the P. acidilactici CCFM6432 obtained in Example 1 was inoculated into an MRS liquid medium and cultured at 37° C. for 16 h to obtain an activated solution with the bacterial concentration of $1 \times 10^7$ CFU/mL. The activated solution was inoculated into the MRS liquid medium according to the inoculum amount of 1% (v/v), and cultured at 37° C. for 16 h to obtain a primary seed solution. The primary seed solution was inoculated into the MRS liquid medium according to the inoculum amount of 1% (v/v), and cultured at 37° C. for 16 h to obtain a secondary seed solution. The secondary seed solution was inoculated into the MRS liquid medium at the inoculum amount of 1% (v/v) and cultured at 37° C. for 16 h to obtain a bacterial solution. The bacterial solution was centrifuged at 6000 g for 15 min, and precipitate was collected. The precipitate was washed twice with a PBS buffer with the pH of 7.4, and then centrifuged again at 6000 g for 10 min to obtain bacteria. The P. acidilactici CCFM6432 bacteria were resuspended to the cell concentration of $1 \times 10^{10}$ CFU/mL with a protective agent solution containing 130 g/L skim milk, 20 g/L trehalose, and 20 g/L sucrose to obtain a P. acidilactici CCFM6432 bacterial suspension, which can be taken as an oral liquid preparation. The P. acidilactici CCFM6432 bacterial suspension was freeze-dried to obtain P. acidilactici CCFM6432 bacterial powder. Stearic acid as a lubricant accounting for 2% of the total weight of the bacterial powder and sodium carboxymethyl cellulose (CMC-Na) as a binder accounting for 3% of the total weight of the bacterial powder were added to the P. acidilactici CCFM6432 bacterial powder to obtain tablets.

According to the methods of Examples 2 to 7, the effects of the fermented food prepared in Example 9 and the drugs prepared in Example 10 were respectively verified. The results show that the prepared fermented food or drugs could alleviate depression-like behaviors of mice caused by stress, increase the content of neurotransmitter (5-HT) in the brain tissue of the depressed mice, promote biosynthesis of the neurotransmitter precursor (5-HTP) in the peripheral tissue, inhibit excessive secretion of corticotropin releasing factors (CRF) in the hypothalamus, and reduce the level of corticosterone in the serum; the fermented food could regulate the immunity of the host, increase the proportion of regulatory T cells in the spleen, decrease the concentration of proinflammatory factors IL-1β, IL-6 and TNF-α in the serum; and the fermented food also could improve the diversity of the intestinal microbiome, restore intestinal microbiome disorders caused by stress, increase the abundance of probiotics (Bacillus and Coprococcus), increase the content of butyric acid in the intestine, and reduce the risk of inflammatory bowel disease, obesity and type II diabetes.

Although the disclosure has been disclosed as above in preferred examples, it is not intended to limit the disclosure. Anyone skilled in the art can make various changes and modifications without departing from the spirit and scope of the disclosure. Therefore, the protection scope of the disclosure should be defined by the claims.

What is claimed is:

1. A method for treating depression, comprising:
 administering a probiotic preparation comprising *Pediococcus acidilactici* CCFM6432 to an individual in need thereof,
 wherein the CCFM6432 strain is preserved at the Guangdong Microbial Culture Collection Center with the number 60638, and
 wherein the individual suffers from or has been diagnosed with depression.

2. The method of claim 1, wherein the probiotic preparation is $1\times10^5$ CFU/mL, or $1\times10^5$ CFU/g or more of the *Pediococcus acidilactici* CCFM6432.

3. A drug comprising:
 a freeze-dried bacterial powder formulation,
 a lubricant, and
 a binder,
 wherein the freeze-dried bacterial powder formulation is prepared from a mixture of *Pediococcus acidilactici* CCFM6432 and a protective agent solution comprising skim milk, trehalose, and sucrose,
 wherein the lubricant comprises stearic acid, and
 wherein the binder is sodium carboxymethyl cellulose.

4. The drug of claim 3, wherein the drug is in a form of a tablet, a powder, or an oral liquid.

5. A drug comprising:
 a freeze-dried bacterial powder formulation,
 a lubricant, and
 a binder,
 wherein the freeze-dried bacterial powder formulation is prepared from a mixture of *Pediococcus acidilactici* CCFM6432 and a protective agent solution comprising 130 g/L skim milk, 20 g/L trehalose, and 20 g/L sucrose,
 wherein the lubricant comprises stearic acid, and
 wherein the binder is sodium carboxymethyl cellulose.

6. The drug of claim 5, wherein the drug is in a form of a tablet, a powder, or an oral liquid.

* * * * *